United States Patent [19]

Fleischer et al.

[11] Patent Number: 5,635,628
[45] Date of Patent: Jun. 3, 1997

[54] METHOD FOR DETECTING METHANE IN A GAS MIXTURE

[75] Inventors: Maximilian Fleischer, Hoehenkirchen; Hans Meixner, Haar, both of Germany

[73] Assignee: Siemens Aktiengesellschaft, Munich, Germany

[21] Appl. No.: 635,517

[22] Filed: Apr. 22, 1996

[30] Foreign Application Priority Data

May 19, 1995 [DE] Germany .................. 195 18 547.1

[51] Int. Cl.⁶ ............ G01N 27/00; G01N 31/12; G01N 27/12
[52] U.S. Cl. ............ 73/31.06; 73/23.2; 73/23.31; 422/83; 422/98
[58] Field of Search ............ 73/31.06, 23.2, 73/23.31, 31.03; 422/83, 94, 98

[56] References Cited

U.S. PATENT DOCUMENTS

| 4,535,315 | 8/1985 | Sakai | 338/34 |
|---|---|---|---|
| 4,569,826 | 2/1986 | Shiratori et al. | 422/90 |
| 4,587,104 | 5/1986 | Yannopoulos | 422/94 |
| 4,706,493 | 11/1987 | Chang et al. | 73/23 |
| 4,840,913 | 6/1989 | Logothetis et al. | 436/116 |
| 4,892,834 | 1/1990 | Raul | 436/149 |
| 4,911,892 | 3/1990 | Grace et al. | 422/94 |
| 5,055,266 | 10/1991 | Stetter et al. | 422/83 |
| 5,071,626 | 12/1991 | Tuller | 422/98 |
| 5,296,196 | 3/1994 | Takeshima | 422/98 |
| 5,330,719 | 7/1994 | Barnett et al. | 422/95 |
| 5,374,400 | 12/1994 | Sprinkle et al. | 422/94 |
| 5,445,796 | 8/1995 | Mori | 422/98 |
| 5,476,003 | 12/1995 | Neumann | 73/31.06 |

FOREIGN PATENT DOCUMENTS

| 0 603 945 A1 | 6/1994 | European Pat. Off. . |
| 43 10 914 A1 | 10/1994 | Germany . |
| WO94/23288 | 3/1994 | WIPO . |

OTHER PUBLICATIONS

Patent Abstract of Japan, P–200, Mar. 12, 1983, vol. 7, No. 125, for JP 58 042962, 31 May 1983, Detection Apparatus of Combustible Gas, Koga Kouichi, 1 sheet.
Patent Abstract of Japan, P–159, Sep. 1, 1982, vol. 6, No. 245, for JP 57 141543, 3 Dec. 1982, Gas Sensor, Mitsuyoshi Takahiko, 1 sheet.
Patent Abstract of Japan, P–154, Aug. 9, 1982, vol. 6, No. 225, for JP 57 127839, 10 Nov. 1982, Gas Detecting Element, Kimura Ikuhiko, 1 sheet.
Patent Abstract of Japan, P–787, Jul. 9, 1988, vol. 12, No. 436, for JP 63 165746, 17 Nov. 1988, Gas Sensor, Fujiyama Seiji; others; 01, 1 sheet.

*Primary Examiner*—Hezron E. Williams
*Assistant Examiner*—J. David Wiggins
*Attorney, Agent, or Firm*—Hill, Steadman & Simpson

[57] ABSTRACT

A method and apparatus for detecting methane in a gas mixture that may contain commonly used solvents including alcohols and acetones is provided which measures a change in electrical resistivity, electrical conductivity or relative permeability caused by the presence of methane gas at a chemically active sensing structure. The apparatus includes two spaced-apart electrodes that are covered with a thin methane-sensitive semi-conductive metal oxide layer. The gas to be tested is heated to a temperature exceeding 740° C. before it contacts the metal oxide layer. Alcohols, acetones and other solvents are oxidized to electrical carbon dioxide and water before they reach the metal oxide layer so that only the less reactive and reducing gas methane reaches the metal oxide layer where it is reduced and increases the conductivity of the metal oxide layer as measured between the two spaced-apart electrodes with an appropriate electrical meter instrument.

20 Claims, 7 Drawing Sheets

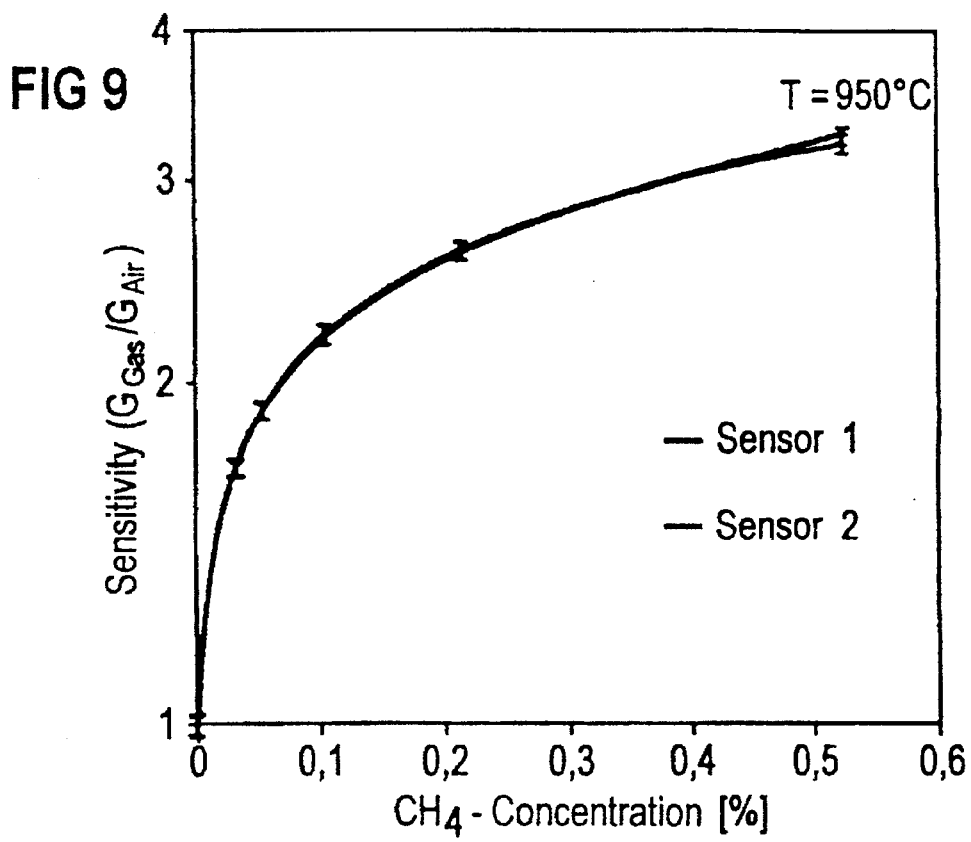
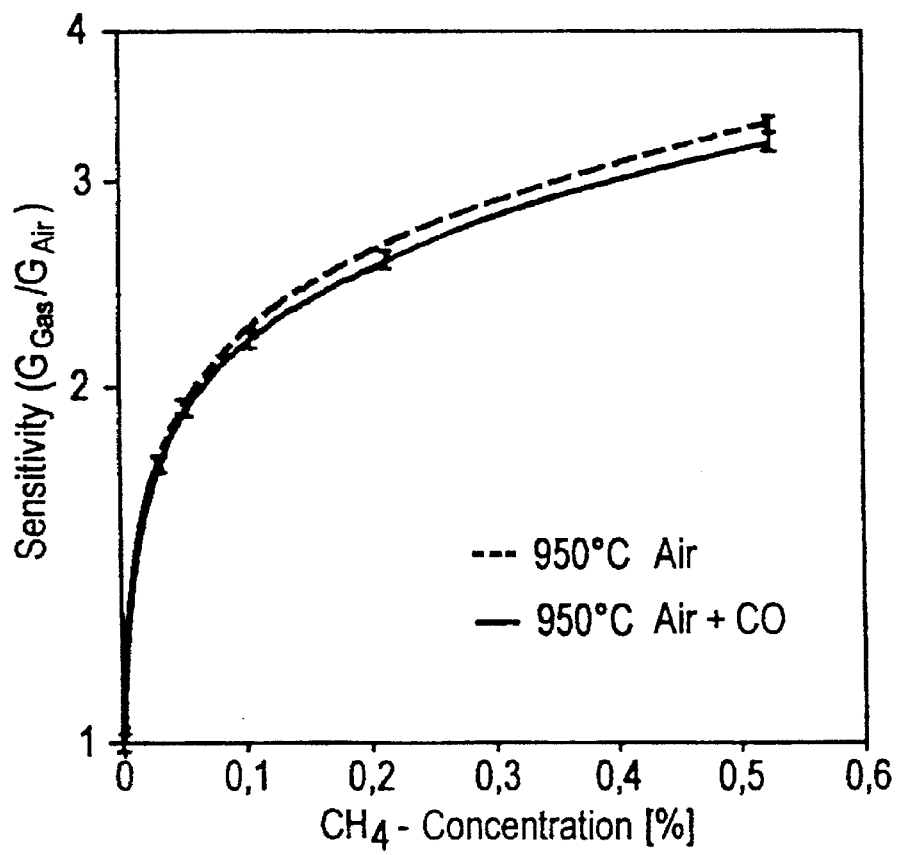

METHOD FOR DETECTING METHANE IN A GAS MIXTURE

BACKGROUND OF THE INVENTION

1. Field of the Invention

This invention relates to gas sensors. More specifically, this invention relates to method and apparatus for detecting methane in a gas mixture also containing known interference gases.

2. Description of the Prior Art

Sensors for the detection of methane in air are known. Currently available methane sensors typically utilize semiconducting metal oxides. Also, reaction heat sensors or heat tone sensors called pellistors are also used to detect methane.

The metal oxide most often used as a sensor material is tin oxide, which is a semiconductor at higher temperatures. A tin oxide sensor that has been doped with platinum will react to the presence of methane and other reducing gases. The operating temperature of a Pt-doped $SnO_2$ sensor is typically low, around 350° C.

Another methane sensor known in the art has a thin film of $Ga_2O_3$ as a gas-sensitive element. At temperatures greater than 700° C., a $Ga_2O_3$ sensor will generate a very strong measurement signal even when the methane concentration is well below the lower explosive limit of 5%. The $Ga_2O_3$ sensor does not react to the presence of water vapor in air. However, like all known $SnO_2$ sensors and pellistors, the $Ga_2O_3$ sensors are extremely sensitive to the presence of alcohols. The reaction of a $Ga_2O_3$ sensor to the presence of alcohol—a commonly used solvent—is called cross-sensitivity, and in some circumstances, will completely mask the reaction of the $Ga_2O_3$ sensor to methane.

Therefore, a need exists for an improved methane gas sensor which is useful at high temperatures and in the presence of commonly used solvent vapors.

SUMMARY OF THE INVENTION

The method of the present invention enables the construction of gas warning devices by means of which the concentration of methane in air can be continuously monitored. Such devices can be used in areas where known methane sensors often set off false alarms due to alcohol vapors and/or other solvent vapors present in the air.

In one method for detecting methane gas in accordance with the present invention, the gas to be tested is heated to a temperature exceeding 740° C. before it is exposed to a methane-sensitive metal oxide whose temperature exceeds 740° C. The gas is preheated to oxidize any solvents present in the gas. Changes in the resistivity, conductivity or relative permeability of the metal oxide layer are then measured to detect the reaction between the methane and the metal oxide layer.

In an embodiment, a methane sensor is provided which includes two spaced-apart electrodes that are covered by a methane-sensitive semi-conducting metal oxide film. A means for heating the gas to be tested and metal oxide film to a temperature exceeding 740° C. is provided. A means for measuring changes in the resistivity, conductivity or permeability of the metal oxide is used to detect a reaction between methane and the metal oxide film.

An advantage of the invention is the creation of a method and apparatus by which methane can be unambiguously detected in a gas mixture containing solvent vapors.

DESCRIPTION OF THE DRAWINGS

The invention is illustrated diagrammatically in the accompanying figures wherein:

FIG. 9, illustrates, graphically, the methane sensitivity of a $Ga_2O_3$ sensor layer fabricated in accordance with the present invention; and FIG. 10, illustrates, graphically the carbon monoxide cross-sensitivity of the $Ga_2O_3$ sensor layer.

DESCRIPTION OF THE PREFERRED EMBODIMENTS

Due to the $sp^3$-hybridization of its electron orbits, the methane molecule has a tetrahedral structure. Methane is thus chemically more stable than the molecules of organic solvents especially in regards to a tendency to resist oxidation, even at high temperatures. The invention exploits this characteristic for the detection of the comparatively less reactive methane, without disturbing cross-sensitivities, in a gas mixture containing solvent vapors by means of the sensor schematically represented in FIG. 1.

Figure 2:
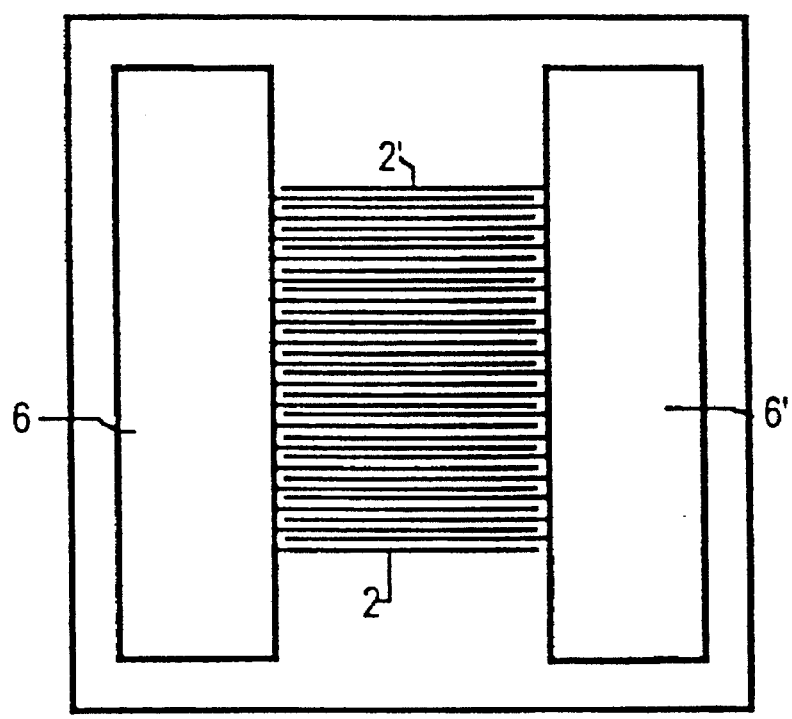
FIG. 2 is a top view of the comb electrodes of a methane sensor fabricated in accordance with the present invention.

The main body 1 of the sensor, which is about 0.5 μm thick, is made of an electrically insulating temperature-stable material such as beryllium oxide, aluminum oxide or silicon. Two platinum electrodes 2, 2', a $Ga_2O_3$ thin film 3 as a $CH_4$-sensitive element that conductively connects the comb electrodes 2, 2', and a temperature probe 4 are arranged on the main body 1. An $SiO_2$ passivation layer 5 is intended to shield the connection leads 6, 6' which extend from the two comb electrodes 2, 2' and the leads 7, 7' which extend from the temperature probe 4, from the oxygen present in the gas being tested. The dimensions of the comb electrodes 2, 2' depend on the specific resistance of the sensor layer 4 in the desired temperature region. The sensor layer 4 is manufactured by means of a sputtering or vacuum evaporation process and has a thickness from about 1 μm to about 2 μm. The electrodes 2, 2' of the interdigital structure, shown to scale in a top view in FIG. 2, can comprise thicknesses from about 0.1 to about 10 μm, widths from about 1 to about 1000 μm and spacings from about 1 to about 100 μm.

Figure 3:
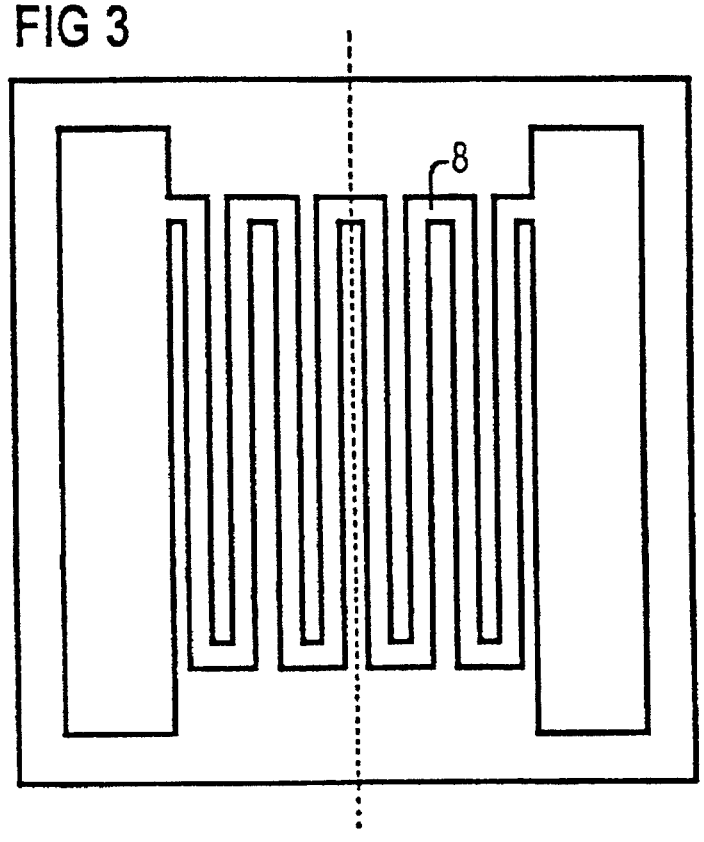
FIG. 3 is a bottom view of the sensor shown in FIG. 2, particularly illustrating the resistance heating means.

In order to enable the operating temperature, which is preferably between 700° C. and 1000° C., to be set and held constant independent of external influences, the sensor 1 is actively heated by a resistance layer 8, which is arranged on the back side of the main body 1, which is passivated if warranted. This resistance layer 8 is shown to scale in FIG. 3 and is preferably made of platinum, gold or an electrically conductive ceramic.

Figure 4:
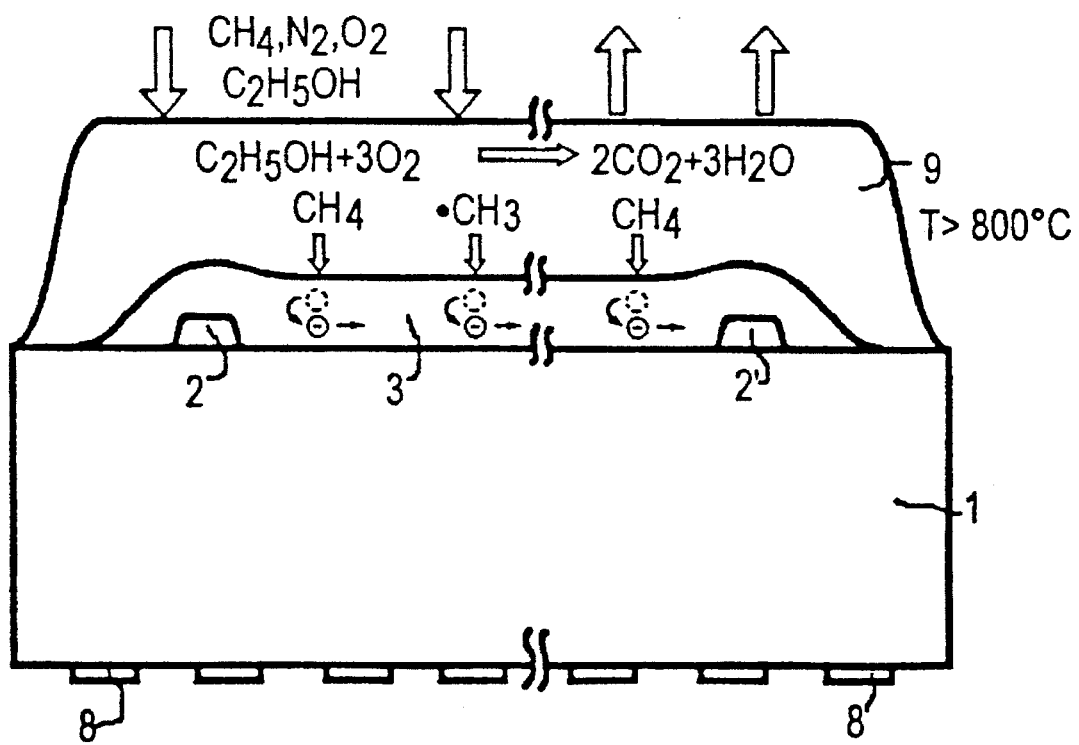
FIG. 4 is a sectional view taken through the gas-sensitive area and the covering layer of a methane sensor fabricated in accordance with the present invention.
Figure 8:
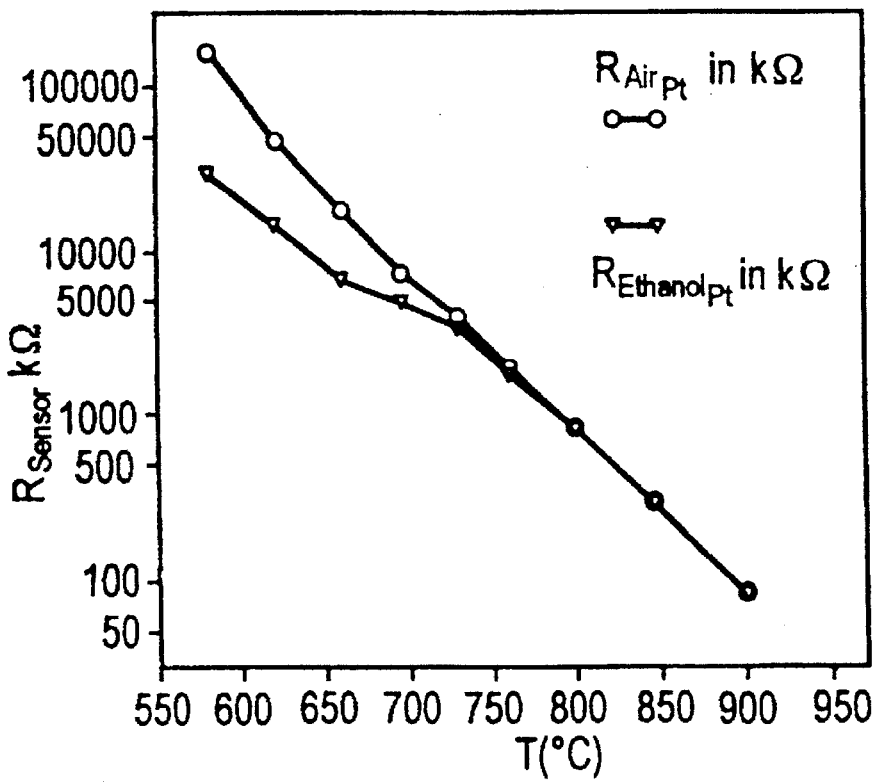
FIG. 8, illustrates, graphically, the alcohol sensitivity of a Pt-doped $Ga_2O_3$ sensor layer fabricated in accordance with the present invention.

The porous layer 9, which is shown in FIG. 4, completely covers the $CH_4$-sensitive element 3. In porous layer 9, the comparatively reactive organic solvents (e.g., alcohol and acetone) are oxidized to the products $CO$, $CO_2$ or $H_2O$ before reaching the thin film 3. Therefore, the reactive organic solvents do not influence the conductivity of the $Ga_2O_3$ because these components are oxidized before they reach the layer 3. The oxidation of the solvents takes place at a temperature predetermined by the heating element 8. One suitable temperature is about 800° C. or higher. As shown in FIG. 8, when a dopant, such at Pt, is utilized, the solvent vapors will be oxidized at a lower temperature of about 740° C. In contrast, the less active methane is not oxidized at these temperatures.

Therefore, the methane reaches the surface of the $Ga_2O_3$ thin film 3 and reacts there with the oxygen of the metal oxide. The oxygen vacancies that arise emit electrons to the crystal lattice, so that the conductivity of the $Ga_2O_3$ thin film 3 increases according to the concentration of methane in the gas being tested. Due to the high temperature (greater than 800° C.) in the covering layer 9, which is about 1 to 50 μm thick, in particular 10 μm, the methane is partially converted by cracking processes into more reactive constituents which reach the thin film 3, and change its conductivity more than methane itself thereby yielding an enhanced sensor response.

Figure 11:
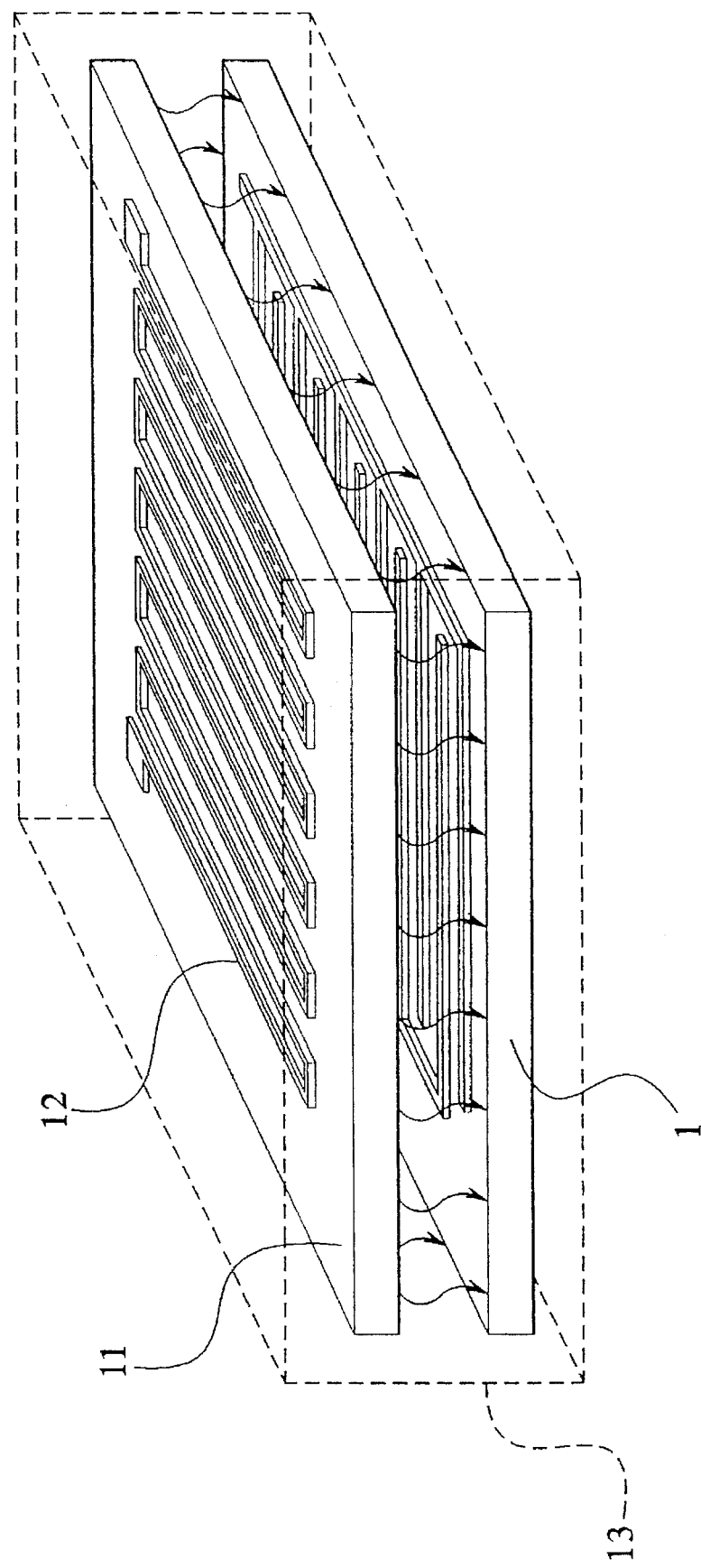
FIG. 11 is a perspective view of a methane sensor fabricated in accordance with the present invention, particularly illustrating a thin film heater disposed above the metal oxide layer as well as an insulating housing shown in phantom.

The covering layer 9 is made of an electrically non-conductive, temperature-stable material, whereby in particular $SiO_2$, SiN or SiON (silicon oxinitride) in polycrystalline or amorphous form, as well as non-conductive ceramics (e.g. ceramics based on the metal oxides $Al_2O_3$ and BeO) or combinations of the cited materials are suitable. The porous layer 9 serves as a covering layer over the metal oxide sensing layer of FIG. 4. The depositing of the covering layer 9 may for example be achieved by means of silk-screen printing techniques, sedimentation, precipitation or vacuum coating. The effect of the covering layer 9 is improved by providing it with a dispersion of oxidation catalysts such as Pt, Pd or $Fe_2O_3$. As an alternative to the porous layer 9, a housing or thin heating layer may be provided for heating of the test gas before it reaches the metal oxide layer 3. FIG. 11 illustrates a main body 1 of a methane sensor disposed beneath a thin heating layer 11 which, in the embodiment illustrated in FIG. 11, is a thin film heating resistance layer. Current flows through the electrode 12 which results in infrared radiation extending downward to the sensor body 1. Alternatively, an insulated housing 13 may be provided as an alternative to or in addition to the heating layer 11. The housing 13 preferably includes a heating element such as an electrode in order to heat the space inside the housing within which the sensor body 1 is located.

RESULTS

Figure 1:
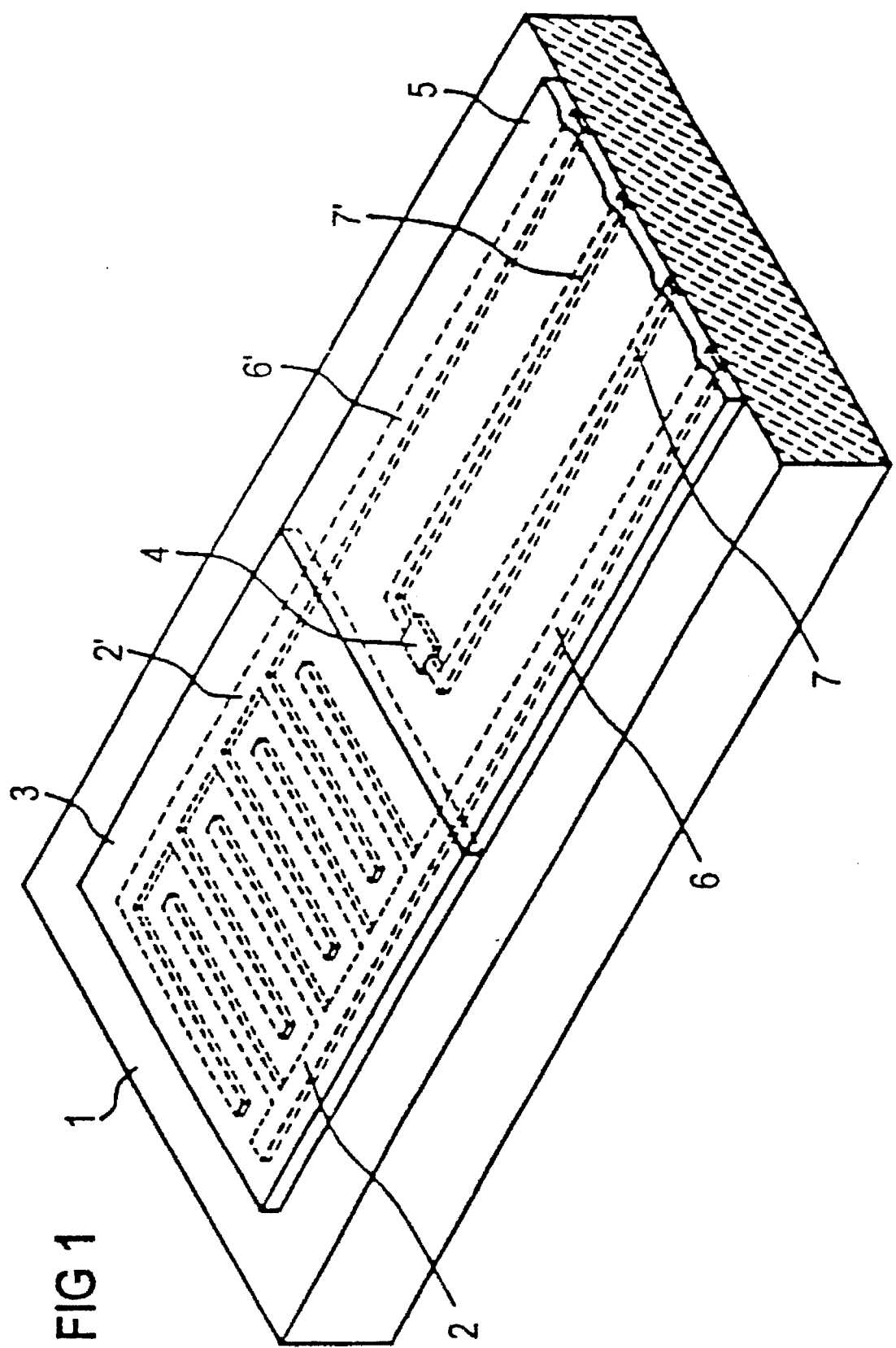
FIG. 1 is a perspective view of a methane sensor fabricated in accordance with the present invention.

In order to determine the extent the preheating of the gas to be detected causes the desired oxidation of the organic solvents (alcohol or acetone), the $Ga_2O_3$ sensor represented in FIG. 1 was arranged in a test chamber of a high-temperature oven and exposed to solvent vapors. In a first series of tests, the hot air supplied to the sensor contained 1000 ppm ethanol, and in a second series it contained 1000 ppm acetone. The gas temperatures corresponded to the sensor temperature. The sensitivities are defined as the ratio of the resistance measured for air divided by the resistance measured for the air including the solvent vapors, e.g.

$R_{air}/R_{ethanol}$ or, respectively, $R_{air}/R_{acetone}$ where $R_{air}$=sensor resistivity to air $R_{ethanol}$=sensor resistivity to air +1000 ppm ethanol $R_{acetone}$=sensor resistivity to air +1000 ppm acetone.

Figure 5:
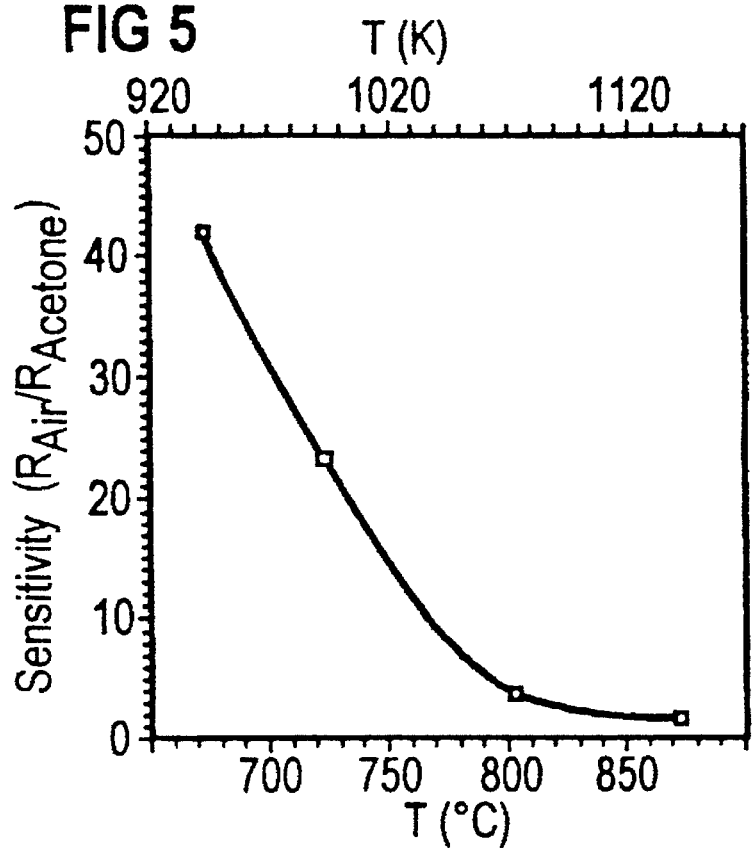
FIG. 5 illustrates, graphically, the alcohol sensitivity at varying temperatures of a $Ga_2O_3$ sensor, fabricated in accordance with the present invention.
Figure 6:
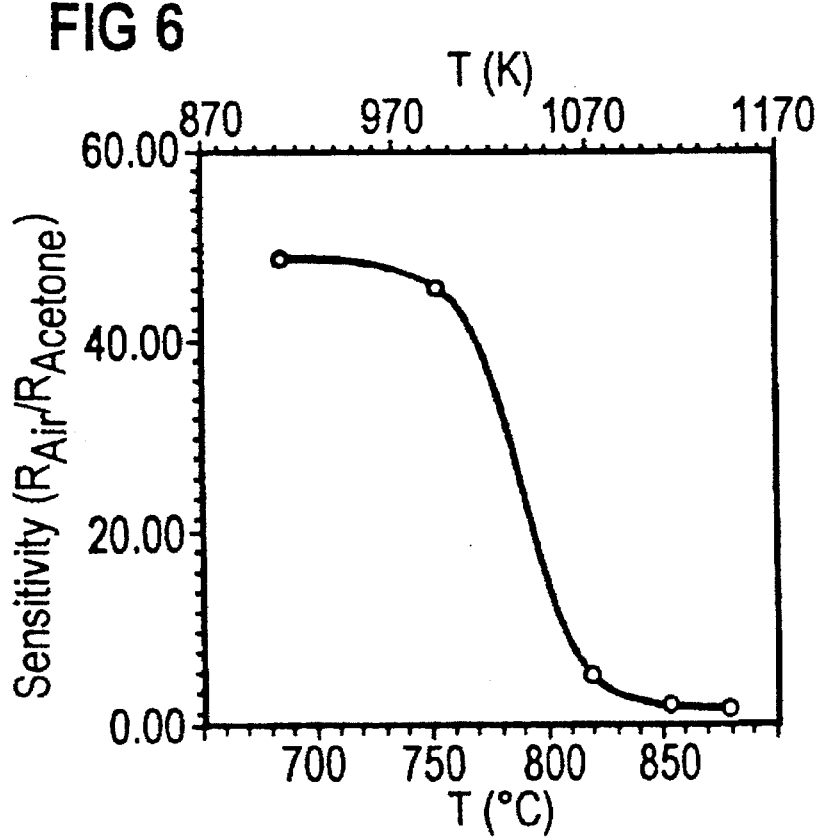
FIG. 6 illustrates, graphically, the acetone sensitivity at varying temperatures of a $Ga_2O_3$ sensor, fabricated in accordance with the present invention.

The corresponding measurement curves are illustrated in FIGS. 5 and 6. It is clearly illustrated that the cross-sensitivity of the $Ga_2O_3$ thin film to ethanol and acetone approaches zero as the gas temperatures exceed 800° C. A mass spectroscopic analysis of the gas flowing through the test chamber confirmed the suspected conversion of the alcohol into $CO_2$ and $H_2O$.

Figure 7:
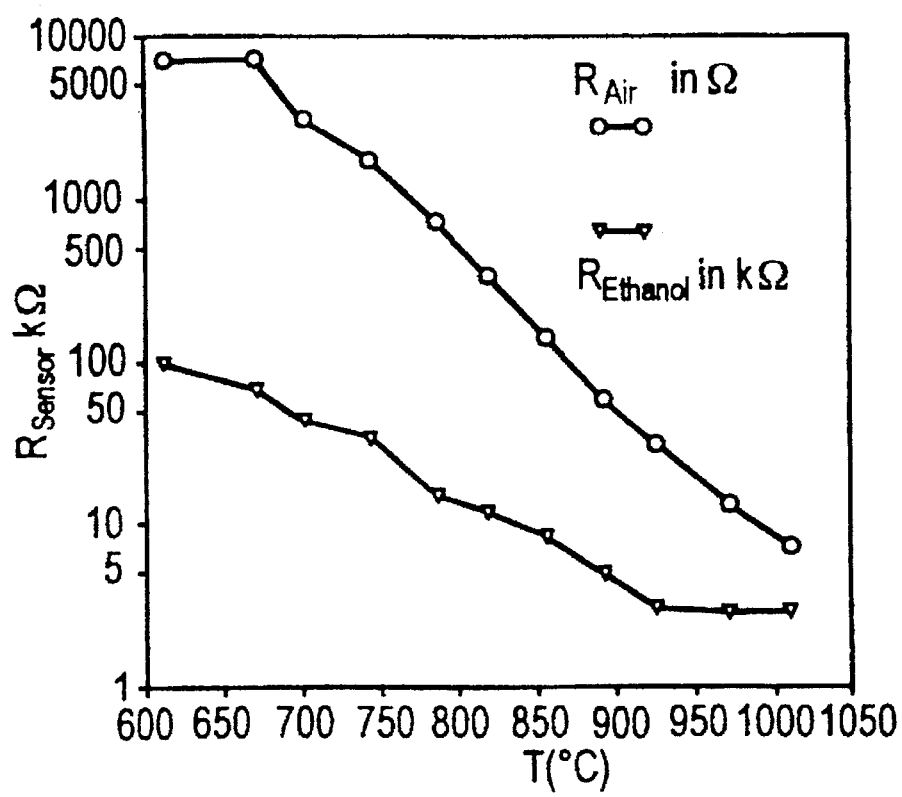
FIG. 7 illustrates, graphically, the alcohol sensitivity of an untreated or non-Pt-doped $Ga_2O_3$ sensor layer fabricated in accordance with the present invention.

As shown in FIGS. 7 and 8, the oxidation of the solvent can also be achieved by a catalytic activation of the sensor surface as opposed to oxidation of the solvent in a porous layer. Turning to FIG. 7, the $Ga_2O_3$ thin film that is not doped with Pt displays the expected sensitivity to alcohol. In contrast, referring now to FIG. 8, the $Ga_2O_3$ thin film treated with a Pt dispersion no longer reacts to ethanol at a temperature approaching 740° C.

As shown in FIG. 9, the $Ga_2O_3$ thin film sensor of the present invention is very sensitive to methane. The conductance value thus changes by a factor of three, even if the air contains only 0.4% methane. Further, as shown in FIG. 10, a concentration of 1000 ppm CO, well above the MAC value, influences the measurement signal of the $Ga_2O_3$ sensor of the present invention only insignificantly.

The invention is of course not limited to the exemplary embodiments specified above. The covering layer 9 for heating the gas under test can thus be omitted if the sensor is arranged in a housing that permits the exchange of gases, such a housing would need to be heated. It is further possible to arrange a thin layer provided with a heating resistance layer parallel to the sensor surface. The air gap between the thin layer and the sensor surface would ensure the heating of the test gas and the required gas exchange. It can be advantageous to provide the surface on the sensor side of the thin layer with a catalytically active layer or, respectively, dispersion of a noble metal such as Pt or Pd or of a subgroup metal oxide such as $Fe_2O_3$.

In place of $Ga_2O_3$, the oxygen-sensitive semiconducting metal oxides $TiO_2$, $Fe_2O_3$, $CeO_3$, $SrTiO_3$, $Nb_2O_3$ or $HfO_2$ may also in particular be used in order to measure their methane-concentration-dependent resistance, conductance or relative permeability.

Although modifications and changes may be suggested by those skilled in the art, it is the intention of the inventors to embody within the patent warranted hereon all changes and modifications that reasonably and properly come within the scope of their contribution to the art.

We claim as our invention:

1. Method for detecting methane in a gas mixture, the method comprising the following steps:

heating the gas mixture to a temperature exceeding 740° C.;

exposing the gas mixture to a methane-sensitive semiconducting metal oxide at a temperature exceeding 740° C.; and measuring at least one of resistance, conductivity and relative permeability of the metal oxide as an indicator for methane.

2. The method of claim 1, comprising the further step of:

providing a porous layer that covers the metal oxide in which said gas mixture is present; and wherein the steps of heating the gas mixture comprises heating the gas mixture in said porous layer.

3. The method of claim 2, wherein the step of providing said porous layer includes making the porous layer from material selected from the group consisting of $SiO_2$, SiN or SiOn, a non-conductive ceramic containing $Al_2O_3$ and a non-conductive ceramic containing BeO.

4. The method of claim 1, wherein the step of heating the gas mixture comprises heating the gas mixture to a temperature exceeding 800° C.

5. The method of claim 1, wherein the step of exposing the gas mixture to metal oxide further comprises maintaining said metal oxide at a constant temperature ranging from about 800° C. to about 1000° C.

6. The method of claim 1, wherein the metal oxide comprises a metal oxide selected from the group consisting of $Ga_2O_3$, $TiO_2$, $Fe_2O_3$, $CeO_3$, $SrTiO_3$, $Nb_2O_3$ and $HfO_2$.

7. The method of claim 1, wherein the porous layer includes an oxidation catalyst.

8. The method of claim 7, wherein the oxidation catalyst is Pt.

9. The method of claim 1, wherein the metal oxide layer includes an oxidation catalyst.

10. The method of claim 9, wherein the oxidation catalyst is Pt.

11. An apparatus for sensing the presence of methane in a gas mixture, the apparatus comprising:

a main body including a first surface which includes two spaced-apart electrodes, the electrodes having a covering of a film of an methane-sensitive semi-conducting metal oxide, means for heating the metal oxide film and the gas mixture to a temperature exceeding 740° C., means for measuring at least one of resistance conductivity and relative permeability of the metal oxide film between the two electrodes as an indicator for methane.

12. The apparatus of claim 11, wherein the metal oxide comprises a metal oxide selected from the group consisting of $Ga_2O_3$, $TiO_2$, $Fe_2O_3$, $CeO_3$, $SrTiO_3$, $Nb_2O_3$ and $HfO_2$.

13. The apparatus of claim 11, wherein the means for heating comprises means for heating the metal oxide film and the gas mixture to a substantially constant temperature exceeding 800° C.

14. The apparatus of claim 11, further comprising:

a porous layer covering the metal oxide film, the porous layer providing a space for heating the gas mixture.

15. The apparatus of claim 14, the porous layer comprises a material selected from the group consisting of $SiO_2$, SiN or SiOn, a non-conductive ceramic containing $Al_2O_3$ and a non-conductive ceramic containing BeO.

16. The apparatus of claim 15, wherein the porous layer includes an oxidation catalyst.

17. The apparatus of claim 16, wherein the oxidation catalyst is Pt.

18. The apparatus of claim 11, wherein the metal oxide film includes an oxidation catalyst.

19. The apparatus of claim 17, wherein the oxidation catalyst is Pt.

20. The apparatus of claim 11, wherein the film of oxygen-sensitive semi-conducting metal oxide is doped with Pt.

* * * * *